United States Patent
Takahara

(10) Patent No.: US 8,408,789 B2
(45) Date of Patent: *Apr. 2, 2013

(54) X-RAY ANALYSIS APPARATUS AND X-RAY ANALYSIS METHOD

(75) Inventor: Toshiyuki Takahara, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 387 days.

This patent is subject to a terminal disclaimer.

(21) Appl. No.: 12/813,049

(22) Filed: Jun. 10, 2010

(65) Prior Publication Data

US 2011/0051894 A1    Mar. 3, 2011

(30) Foreign Application Priority Data

Aug. 28, 2009  (JP) ................................ 2009-198718

(51) Int. Cl.
A61B 6/08 (2006.01)

(52) U.S. Cl. .................. 378/206; 378/63; 378/195

(58) Field of Classification Search .................. 378/195, 378/196, 205, 206, 63
See application file for complete search history.

(56) References Cited

U.S. PATENT DOCUMENTS

| | | | | |
|---|---|---|---|---|
| 6,987,832 B2* | 1/2006 | Koppel et al. | | 378/70 |
| 7,970,101 B2* | 6/2011 | Sakai et al. | | 378/46 |
| 8,000,439 B2* | 8/2011 | Matoba | | 378/46 |
| 2003/0215060 A1* | 11/2003 | Ohzawa | | 378/154 |
| 2006/0088139 A1* | 4/2006 | Nakano et al. | | 378/79 |
| 2010/0046701 A1* | 2/2010 | Matoba | | 378/44 |
| 2011/0013744 A1* | 1/2011 | Nicolosi et al. | | 378/62 |
| 2011/0051894 A1* | 3/2011 | Takahara | | 378/86 |
| 2012/0051507 A1* | 3/2012 | Hasegawa et al. | | 378/44 |

FOREIGN PATENT DOCUMENTS

JP    2007-292476 A    11/2007

* cited by examiner

*Primary Examiner* — Thomas R Artman

(74) *Attorney, Agent, or Firm* — Brinks Hofer Gilson & Lione

(57) ABSTRACT

An X-ray analysis apparatus including: a radiation source configured to irradiate an irradiation point on a sample with radiation; an X-ray detector configured to detect a characteristic X-ray emitted from the sample, and output a signal including energy information about the characteristic X-ray; an analyzer configured to analyze the signal; a sample stage configured to allow placement of the sample thereon; a shifting mechanism being capable of relatively shifting the sample on the sample stage and the radiation source and the X-ray detector with respect to each other; a height measuring mechanism being capable of measuring the height of the irradiation point on the sample; and a controller configured to control the shifting mechanism on the basis of the measured height of the irradiation point on the sample and adjust the distance of the sample with respect to the radiation source and the X-ray detector is used.

11 Claims, 4 Drawing Sheets

X-RAY ANALYSIS APPARATUS AND X-RAY ANALYSIS METHOD

RELATED APPLICATIONS

This application claims priority under 35 U.S.C. §119 to Japanese Patent Application No. 2009-198718 filed on Aug. 28, 2009, the entire content of which is hereby incorporated by reference.

BACKGROUND OF THE INVENTION

1. Technical Field

The present invention relates to an X-ray analysis apparatus and an X-ray analysis method for analyzing a fluorescence X-ray generated from a sample surface.

2. Description of the Related Art

A fluorescence X-ray analysis is performed by irradiating a sample with an X-ray emitted from an X-ray source, detecting a fluorescence X-ray, which is a characteristic X-ray emitted from the sample, with an X-ray detector, then obtaining a spectrum from energy detected therefrom, and then conducting a qualitative analysis or a quantitative analysis on the sample. The fluorescence X-ray analysis allows a non-destructive and rapid analysis on the sample, and hence is widely used in manufacturing processes or in quality control. It allows in recent years X-ray detection with a high degree of accuracy and at a high sensitivity, thereby enabling measurement of minute quantities. Especially, the widespread proliferation of the fluorescence X-ray analysis is expected as an analysis method for detecting harmful substances contained in materials or composite electronic components.

In the related art, in JP-A-2007-292476, for example, a composite apparatus provided with a revolver which allows switching between an objective lens of an optical microscope and an X-ray generator of an X-ray analysis apparatus on the same optical axis is proposed. With this composite apparatus, it is not necessary to move a sample from a position of analysis where the sample is detected by the optical microscope and perform alignment of a position to be analyzed in association with the movement thereof for a subsequent X-ray analysis, and the X-ray analysis may be conducted by irradiating the sample at the same position with a primary X ray from the X-ray generator. With this composite apparatus, observation of the sample is performed while changing the magnification of an objective lens using a revolver, and the alignment in the z-direction (height direction) is set in advance so that the focus position of the objective lens and the focus position of the primary X-ray are brought into alignment with each other.

The technology in the related art still has the following problems. When measuring the sample, it is necessary to adjust the focus position of the objective lens and the focus position of the primary X-ray so as to be in alignment with each other in the z-direction in advance. In the technology described in JP-A-2007-292476, since a sample stage controller is independent, an operator is required to perform the alignment in manual operation. In addition, since the revolver is revolved for switching the objective lens, the operation efficiency is not good. When measuring a sample having significant concavity and convexity, there is a risk of collision of the sample with the objective lens.

SUMMARY OF THE INVENTION

In view of such problems as described above, it is an object of the invention to provide an X-ray analysis apparatus and an X-ray analysis method which allow sample measurement safely with high working efficiency.

In order to solve the above-described problem, the invention employs a configuration and a method described below. In other words, an X-ray analysis apparatus according to the invention includes a radiation source configured to irradiate an irradiation point on a sample with radiation; an X-ray detector configured to detect a characteristic X-ray and a scattered X-ray emitted from the sample and output a signal including energy information about the characteristic X-ray and the scattered X-ray; an analyzer configured to analyze the signal; a sample stage configured to place the sample thereon; a shifting mechanism being capable of relatively shifting the sample on the sample stage and the radiation source and the X-ray detector with respect to each other; a height measuring mechanism being capable of measuring the height of the irradiation point on the sample; and a controller configured to control the shifting mechanism on the basis of the measured height of the irradiation point on the sample and adjust the distance of the sample with respect to the radiation source and the X-ray detector. Accordingly, the height of the sample can be grasped accurately, and the distance of the sample on the sample stage with respect to the radiation source and the X-ray detector can be adjusted.

The X-ray analysis apparatus according to the invention includes a laser displacement sensor.

The X-ray analysis apparatus according to the invention includes the laser displacement sensor employing a triangulation-based system.

The X-ray analysis apparatus according to the invention is characterized in that the optical axis of the radiation irradiated from the radiation source is coaxial with the optical axis of the laser displacement sensor, and the sample is irradiated with the radiation and a laser emitted from the laser displacement sensor. Accordingly, even when the sample has concavity and convexity, the laser can be delivered to the position to be irradiated with radiation, so that the height of the position to be irradiated with radiation can be measured accurately.

The X-ray analysis apparatus includes a sample observation system configured to observe the sample, and a focus switching drive mechanism configured to switch the focus of the sample observation system, and is characterized in that the focus position of the sample observation system is adjusted by controlling the focus switching drive mechanism on the basis of the height of the irradiation point on the sample measured by the height measuring mechanism. Accordingly, the measuring point can be observed.

The X-ray analysis apparatus according to the invention is characterized in that the optical axis of the radiation irradiated from the radiation source, the optical axis of the sample observation system having the focus switching drive mechanism, and the optical axis of a laser displacement sensor are coaxial with respect to each other, and the sample is irradiated with the radiation and a laser emitted from the laser displacement sensor.

The X-ray analysis apparatus according to the invention includes a mirror configured to align the optical axis of the laser displacement sensor in coaxial with the optical axis of the radiation, and a beam splitter configured to align the optical axis of the radiation, the optical axis of the laser displacement sensor, and the optical axis of the sample observation system in coaxial with each other. Accordingly, the three optical axes are aligned coaxially, and hence a compact apparatus which can save the space of installation is obtained.

The X-ray analysis apparatus according to the invention is characterized in that the height measuring mechanism is capable of measuring the height of the irradiation point on the sample in a state in which the sample is placed on the sample stage.

An X-ray analysis method according to the invention includes a step of measuring the height of an irradiation point on a sample by a height measuring mechanism; and a step of positioning the irradiation point by relatively shifting the sample on a sample stage and the radiation source and the X-ray detector with respect to each other by a shifting mechanism, and is characterized in that the step of positioning the irradiation point includes controlling the shifting mechanism on the basis of the measured height of the irradiation point on the sample and adjusting the distance of the sample with respect to the radiation source and the X-ray detector by a controller.

The X-ray analysis method according to the invention includes a step of focusing a sample observation system on the irradiation point by a focus switching drive mechanism, and is characterized in that the step of focusing on the irradiation point includes controlling the focus switching drive mechanism on the basis of the measured height of the irradiation point on the sample and adjusting the focus of the sample observation system on the sample by the controller.

The X-ray analysis method according to the invention includes a step of measuring the height of the irradiation point on the sample by the height measuring mechanism; and a step of conducting measurement and analysis by delivering radiation at the height of the irradiation point on the sample, and is characterized in that the step of conducting measurement and analysis includes correcting parameters used in calculation according to the difference between a standard position of irradiation of the radiation and the heightwise position of the irradiation point when performing the calculation for a quantitative analysis from data obtained by the analyzer. Accordingly, an accurate quantitative analysis is achieved.

According to the invention, following advantages are achieved. By grasping the height of the sample accurately by the height measuring mechanism and adjusting the distance of the sample with respect to the radiation source and the X-ray detector by the controller, sample measurement is achieved safely with high working efficiency.

DETAILED DESCRIPTION OF THE PREFERRED EMBODIMENTS

Referring now to FIG. 1 to FIG. 4, an embodiment of an X-ray analysis apparatus and an X-ray analysis method according to the invention will be described. In the respective drawings used in the description given below, the contraction scale is changed as needed in order to illustrate respective members in recognizable sizes.

Figure 1:
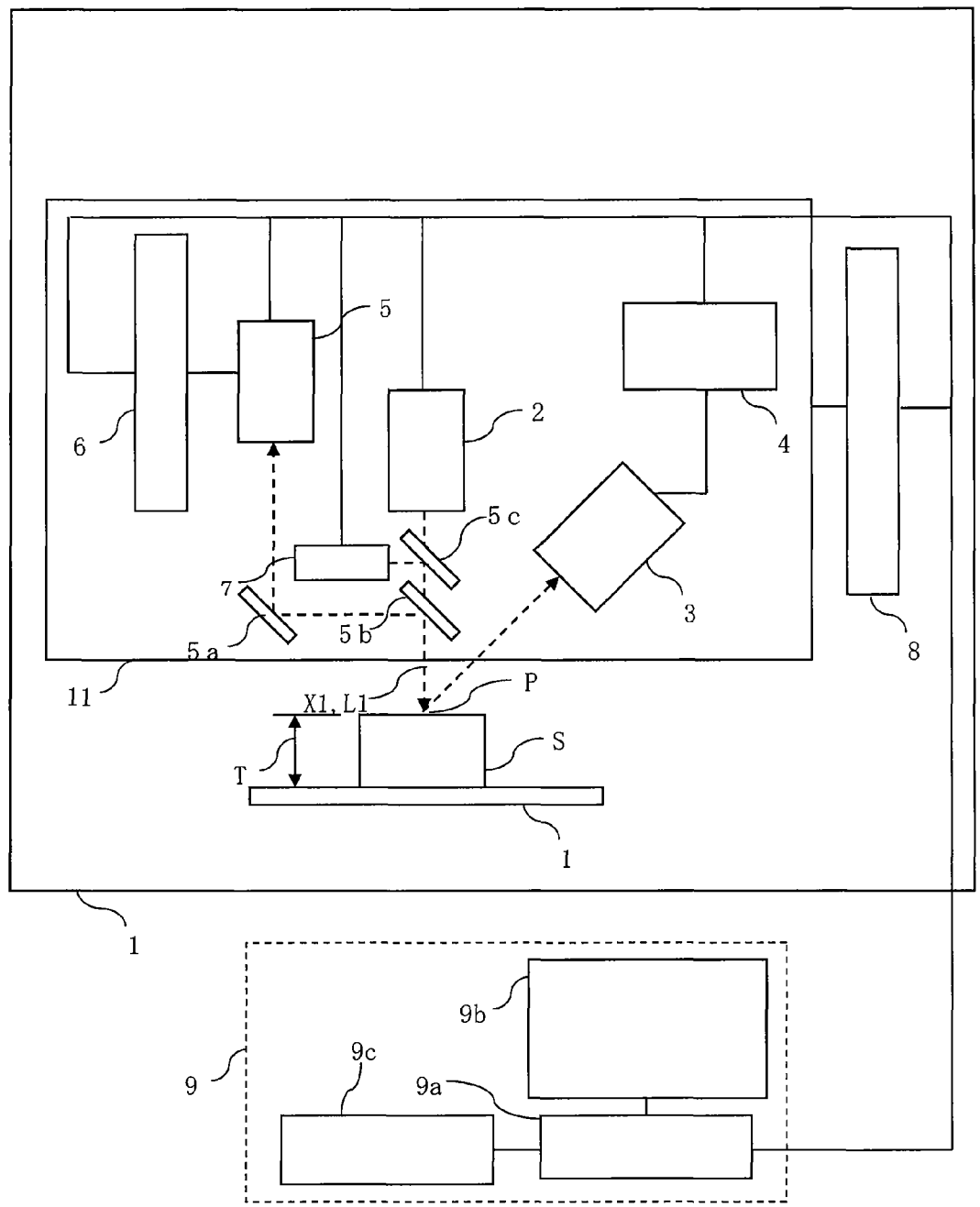
FIG. 1 is a diagrammatic drawing showing an example of general structure of an X-ray analysis apparatus in an embodiment of the X-ray analysis apparatus and an X-ray analysis method.

The X-ray analysis apparatus in this embodiment is, for example, an energy dispersive fluorescence X-ray analysis apparatus and, as shown in FIG. 1, includes a sample stage 1 configured to be movable with a sample S placed thereon, an X-ray tube (radiation source) 2 configured to irradiate a given irradiation point P1 on the sample S with a primary X-ray (radial ray) X1, an X-ray detector 3 configured to detect a characteristic X-ray and a scattered X-ray emitted from the sample S and output a signal including energy information about the characteristic X-ray and the scattered X-ray, an analyzer 4 connected to the X-ray detector 3 and configured to analyze the signal described above, an observational system 5 including an optical microscope or the like configured to acquire an image of the sample S illuminated by an illuminating unit (not shown) as image data, a focus switching drive mechanism 6 configured to move the observational system 5 in the direction of the optical axis thereof for switching the focus position, a measuring head shifting mechanism 8 capable of shifting a measuring head unit 11 including the X-ray tube 2 and the X-ray detector 3 and the sample S on the sample stage 1 with respect to each other, a laser displacement sensor 7 capable of measuring the height of the sample at the given irradiation point P1 on the sample S, and a controller 9 connected to the analyzer 4 and configured to perform an analyzing process for determining the intensity of the X-ray corresponding to a specific element and control respective mechanisms.

The X-ray tube 2 is configured to emit an X-ray generated by collision of thermoelectrons generated from a filament (anode) in the tube and accelerated by a voltage applied between the filament (anode) and a target (cathode) with W (tungsten), Mo (molybdenum), Cr (chrome) and the like as the target through a window formed with beryllium foil or the like as the primary X-ray X1.

The X-ray detector 3 includes a semiconductor detecting element (for example, Si (silicon) element as a pin-structure diode) (not shown) installed at an X-ray entrance window and, if one X-ray photon enters therethrough, generates a current pulse corresponding to the one X-ray photon. A momentary current value of the current pulse is proportional to the energy of the entered characteristic X-ray. The X-ray detector 3 is set to convert the current pulse generated by the semiconductor detecting element into a voltage pulse, amplitude the same, and output the same as a signal.

The analyzer 4 is a pulse height analyzer (multichannel analyzer) configured to obtain the pulse height of the voltage pulse from the above-described signal and generate an energy spectrum.

The observational system 5 includes an optical microscope and an observational camera or the like, which are capable of visually recognizing and imaging an enlarged image or the like of the sample S via a mirror 5a and a beam splitter 5b.

The observational system 5 is capable of switching the focus position continuously using the focus switching drive mechanism 6 for moving the observational system 5 along the optical axis thereof and switching the focus position.

The above-described sample stage 1 is an XY stage which is capable of moving horizontally in four directions in a state in which the sample S is placed thereon.

The measuring head shifting mechanism 8 is capable of shifting the measuring head unit 11 including the X-ray tube 2, the X-ray detector 3, the analyzer 4, the observational system 5, the focus switching drive mechanism 6, and the laser displacement sensor 7 integrally along the direction of travel of the primary X-ray X1. The focus switching drive mechanism 6, the sample stage 1, and the measuring head shifting mechanism 8 employ an actuator such as a ball screw, a belt, connected or built-in, and are driven by a stepping motor or the like.

The laser displacement sensor 7 enables the height of the sample at the given irradiation point P1 on the sample S placed on the sample stage 1 to be measured. A primary laser beam L1 emitted from a laser beam source (not shown) of the laser displacement sensor 7 provided in the vicinity of the X-ray tube (radiation source) 2 is delivered toward the irradiation point via a mirror 5c. At this time, the optical axis of the primary laser beam L1 and the optical axis of the primary X-ray X1 are set to be coaxial. The optical axis of the primary laser beam L1 is coaxial also with the optical axis of the observational system 5. The primary laser beam L1 is delivered to the given irradiation point P1 on the sample S via the beam splitter 5b. A secondary laser beam L2 generated from the irradiation point P1 being irradiated with the primary laser beam L1 goes back to a CCD type light receiving element (not shown) within the laser displacement sensor 7 (not shown), acquires distance (height) information by detecting the sensing state of the returned secondary laser beam L2 on an element to element basis, and the output thereof is fed to the controller 9. The beam splitter 5b and the mirror 5c are of a movable type, and hence are retractable from the course of the primary X-ray X1 during the analysis.

The controller 9 is a computer including a CPU or the like and functioning as a control device for controlling the analyzing process and the respective mechanisms, and includes a controller body 9a configured to determine the intensity of the X-ray corresponding to a specific element from an energy spectrum fed from the analyzer 4, a display unit 9b configured to display the result of analysis on the basis of the determined intensity, and an operating unit 9c which allows entry of respective commands or analysis conditions such as the position of the irradiation point P1. The controller body 9a also has a function to communicate with and control the focus switching drive mechanism 6 and the measuring head shifting mechanism 8.

Figure 2:
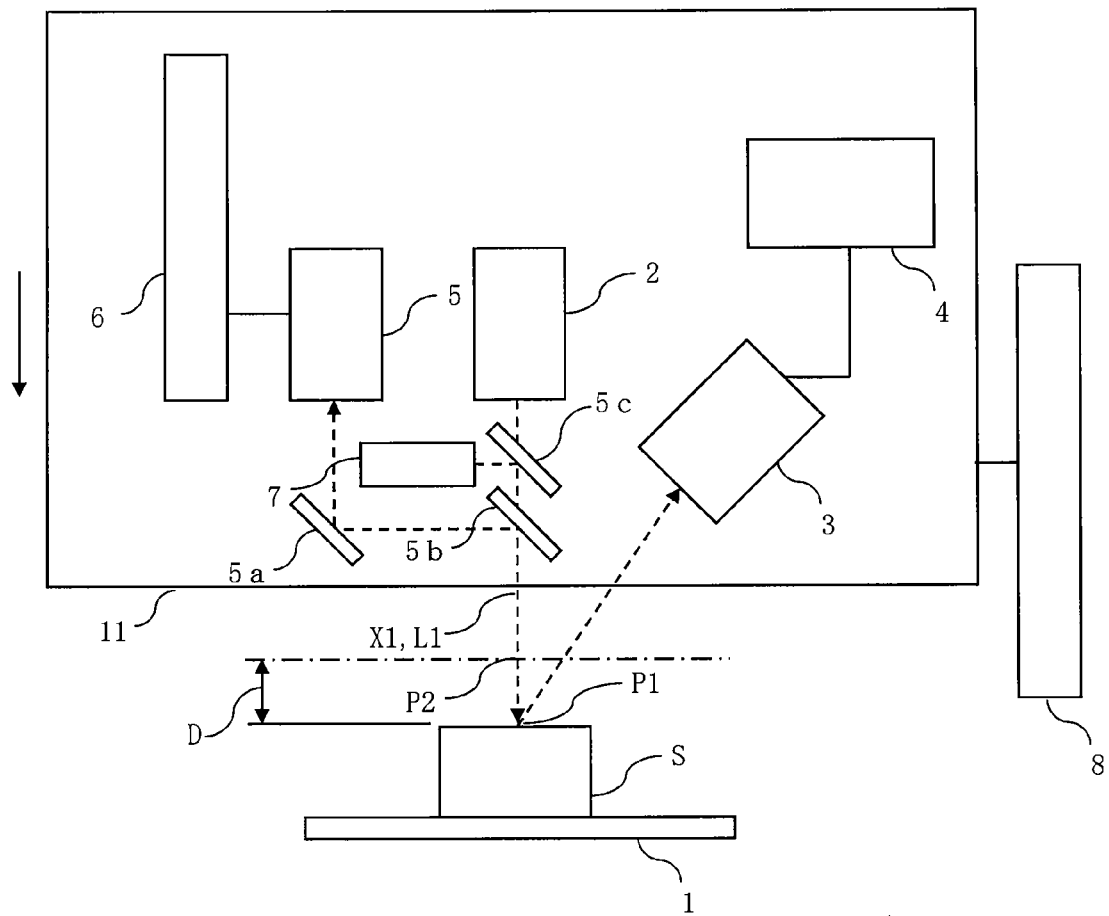
FIG. 2 is an explanatory drawing of an example for explaining a general movement of a shifting mechanism for relatively shifting a sample and a radiation source and an X-ray detector.

The controller body 9a is set to control the measuring head shifting mechanism 8 on the basis of the measured height at the given irradiation point P1 on the sample S and adjust the distance from the sample S to the X-ray tube 2 and the X-ray detector 3 as shown in FIG. 2.

Figure 3:
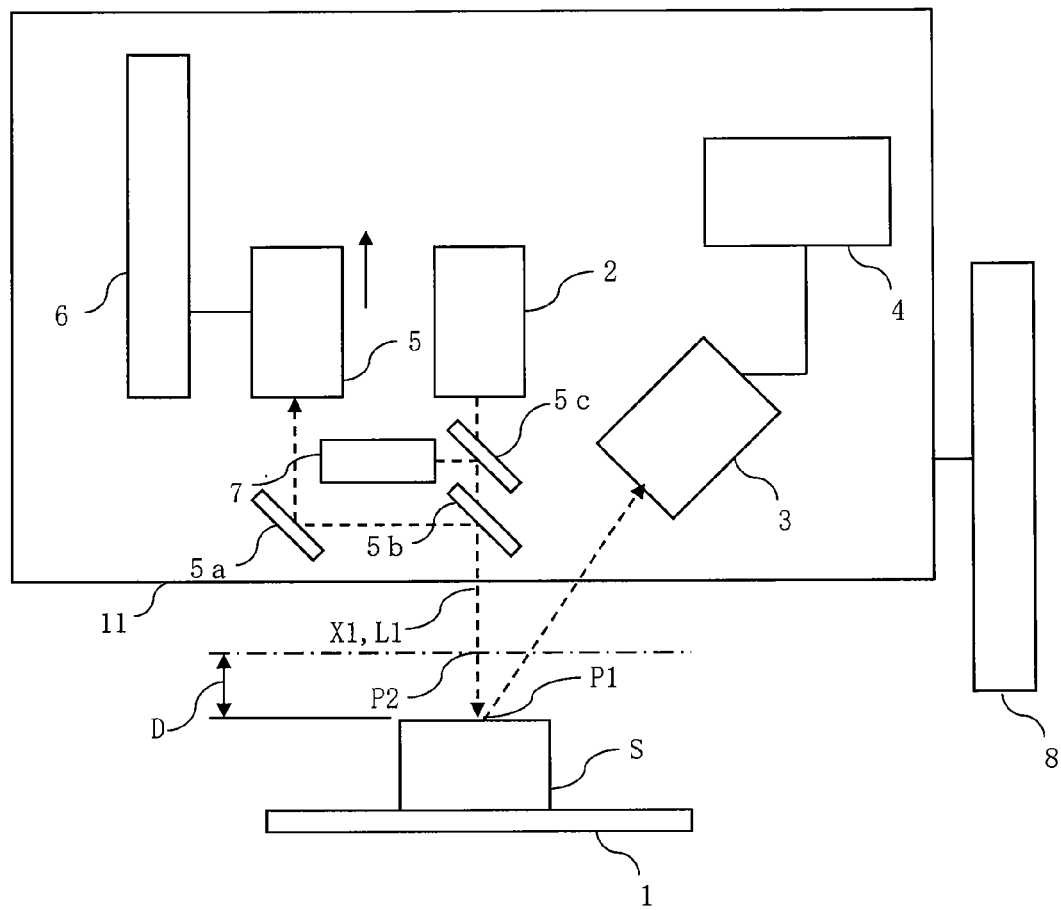
FIG. 3 is an explanatory drawing showing an example for explaining a general movement of a focus switching drive mechanism.

In addition, the controller body 9a is set to control the focus switching drive mechanism 6 on the basis of the measured height of the sample at the given irradiation point P1 on the sample S and adjust the focus position of the observational system 5 as shown in FIG. 3.

The control of the focus switching drive mechanism 6 and the measuring head shifting mechanism 8 by the controller body 9a can be performed simultaneously or independently.

Then, the observational system 5 is configured to be capable of switching the focus continuously with respect to the image of the sample S illuminated with the illuminating unit, not shown, using the focus switching drive mechanism 6 for moving the focus position of the optical microscope or the observational camera or the like of the observational system 5 in the direction of the optical axis thereof. A standard position of irradiation P2 is stored in the controller 9 as the origin position (not shown) of the focus switching drive mechanism 6 in advance. Here, the standard position of irradiation P2 is a position where the irradiation axis of the primary X-ray X1 from the X-ray tube 2 and the direction of the X-ray detector 3 (which provides the best sensitiveness) intersect. By calculating the number of input pulses of the stepping motor or the like for driving the focus switching drive mechanism 6 from the origin position (not shown) and the number of output pulses from an encoder, the distance between the irradiation point P1 on the sample S and the X-ray tube 2 can be obtained. In this manner, the observational system 5 functions also as distance measuring equipment.

The controller 9 is set to obtain a difference between the heightwise position of the sample calculated from the distance obtained by the observational system 5 as the distance measuring equipment and the standard position of irradiation P2, and correct parameters such as an X-ray irradiation distance or the like used by the controller 9 for calculating the determination according to the difference.

In this embodiment, the observation system 5 obtains the distance between the irradiation point P1 and the X-ray tube 2 indirectly by switching and adjusting the focus. However, the distance between the irradiation point P1 and the X-ray detector 3 may be obtained instead.

The sample stage 1, the X-ray tube 2, the X-ray detector 3, the observational system 5, and the laser displacement sensor 7 or the like are stored in a sample chamber 10 which can be depressurized, and the interior of the sample chamber 10 is configured to be depressurized during measurement, so that the X-ray is not absorbed in the ambience in the atmospheric air.

Referring now to FIG. 1 to FIG. 4, an X-ray analysis method using the X-ray analysis apparatus according to this embodiment will be described.

Figure 4:
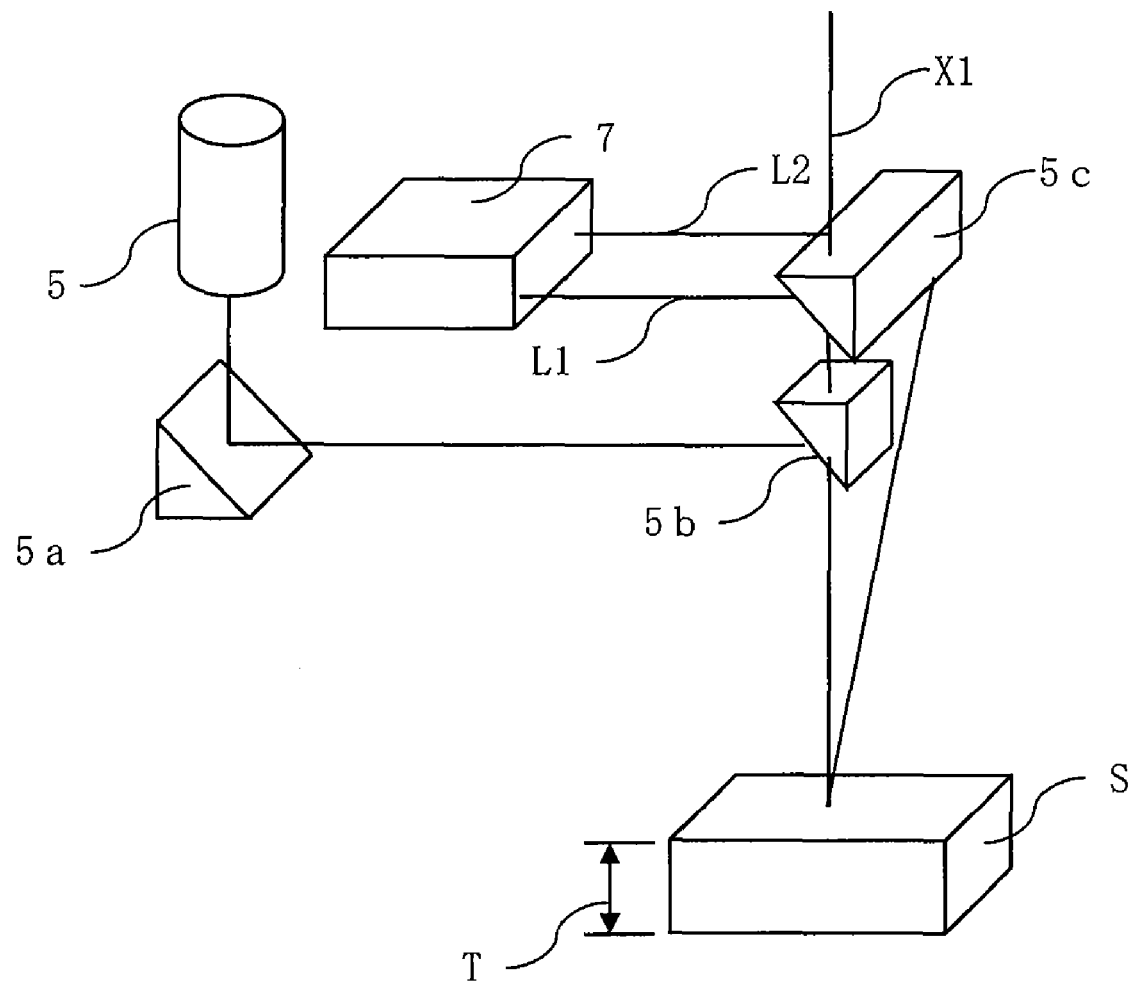
FIG. 4 is an explanatory drawing of an example for explaining a height measuring method for measuring the sample with a triangulation-based laser displacement sensor.

First of all, the sample S is set on the sample stage 1. Then, a height T of the sample S is measured with the laser displacement sensor 7, which is placed so that the primary laser beam L1 is aligned coaxially with the optical axis of the primary X-ray X1 and the optical axis of the observational system 5 in the sample chamber 10 as shown in FIG. 1. In other words, since the primary laser beam L1 emitted from a laser beam source (not shown) of the laser displacement sensor 7 provided in the vicinity of the X-ray tube (radiation source) 2 is coaxial with the optical axis of the primary X-ray X1, it is delivered to the given irradiation point P1 on the sample S via the mirror 5c provided on the optical axis of the primary X-ray X1. The primary laser beam L1 is also coaxial with the optical axis of the observational system 5, and is delivered to the given irradiation point P1 on the sample S via the beam splitter 5b for irradiating the sample S with a laser beam simultaneously. The secondary laser beam L2 generated by irradiation of the sample S with the primary laser beam L1 goes back to the CCD type light receiving element (not shown) in the laser displacement sensor 7 (not shown), so that the distance (height) information is acquired by detecting the sensing state of the returned secondary laser beam L2 on an element to element basis. However, the arrangement is configured such that the secondary laser beam L2 does not pass through the beam splitter 5b so as not to attenuate the intensity of the laser after having returned back from the sample S as shown in FIG. 4.

In addition, the laser displacement sensor 7 outputs the measured height T of the sample S to the controller 9, and the controller 9 memorizes the measured height T of the sample S.

Subsequently, the interior of the sample chamber 10 is brought into a predetermined depressurized state, and the controller 9 activates the sample stage 1 to move the sample S, and places the same right below the X-ray tube 2 for conducting a fluorescence X-ray analysis. In addition, the measuring head unit 11 is moved by the measuring head shifting mechanism 8 to adjust the distance of irradiation of the primary X-ray X1, whereby the irradiation point P1 is set to the position of irradiation of the primary X-ray X1 emitted from the X-ray tube 2.

However, when setting the irradiation point P1, the controller 9 controls the measuring head shifting mechanism 8 on the basis of the measured height T of the sample S and adjusts the distance between the sample S, the X-ray tube 2, and the X-ray detector 3. In other words, as shown in FIG. 2, when the height T of the sample S is lower than the height of the standard position of irradiation P2 of the primary X-ray X1, the controller 9 moves the measuring head unit 11 by an amount corresponding to the distance of a differential D using the measuring head shifting mechanism 8 so as to be brought into alignment with the irradiation point P1, for example.

Furthermore, as shown in FIG. 3, the observational system 5 is also moved by the amount corresponding to the distance of the differential D using the focus switching drive mechanism 6, whereby the focus position of the observational system 5 is also adjusted.

In this manner, by irradiating the sample S with the primary X-ray X1 from the X-ray tube 2 in a state in which the position of the sample S with respect to the X-ray tube 2 and the X-ray detector 3, and the focus position of the observational system 5 are adjusted, the characteristic X-ray and the scattered X-ray generated thereby are detected by the X-ray detector 3.

The X-ray detector 3 having detected the X-ray transmits a signal to the analyzer 4, and the analyzer 4 derives an energy spectrum from the signal and outputs the same to the controller 9.

The controller 9 determines the intensity of the X-ray corresponding to the specific element from the energy spectrum sent from the analyzer 4, and displays the result of analysis on the display unit 9b.

In this case, it is not necessarily required to irradiate the sample S with the primary X-ray X1 at the standard position of irradiation P2. For example, if simpler acquisition of the result of analysis is wanted, analysis at the given irradiation point P1 is also possible. In this event, the controller 9 performs calculation while correcting parameters to be used by the controller 9 in calculation for a quantitative analysis from data on pulse height value of the energy spectrum obtained by the analyzer 4 according to the differential D between the standard position of irradiation P2 and the heightwise position of the irradiation point P1 of the primary X-ray X1. In association with it, the adjustment of the focus position of the observational system 5 is also performed according to the differential D.

In this event, the parameters to be corrected (hereinafter, referred to also as correction parameters) include the distance of the irradiation point P1 from the X-ray tube 2, the distance of the X-ray detector 3 from the irradiation point P1, an angle formed between a line drawn between the X-ray tube 2 and the irradiation point P1 and a line drawn between the irradiation point P1 and the X-ray detector 3.

When there is a difference between the standard position of irradiation P2 and the heightwise position of the irradiation point P1, the distance from the X-ray tube 2 to the irradiation point P1, the distance from the irradiation point P1 to the X-ray detector 3, the orientation of the X-ray detector 3, and the irradiation point P1 vary. Accordingly, the energy density or the irradiation area of the primary X-ray X1 delivered onto the sample S varies. Accordingly, the intensities or the like of the fluorescence X ray emitted from the sample S and the scattered X-ray emitted from the sample S may vary, and also the intensities of the fluorescence X-ray or the scattered X-ray detected by the X-ray detector 3 may vary. Therefore, by calculating with the correction parameter added thereto, an accurate quantitative analysis is achieved.

In this embodiment, since the optical axis of the observational system 5 and the optical axis of the X-ray tube 2 are coaxial in terms of the difference from the heightwise position by using the mirror 5a and the beam splitter 5b, the angle formed between the orientation of the X-ray tube 2 and the irradiation point P1 does not change. However, in the configuration which does not have these members, the optical axis of the observational system 5 is different from the optical axis of the X-ray tube 2, so that a correction parameter for the angle formed between a line drawn between the X-ray tube 2 and the irradiation point P1 and a line drawn between the irradiation point P1 and the X-ray detector 3 is used.

In this manner, in the X-ray analysis apparatus and the X-ray analysis method in this embodiment, since the sample is irradiated with the X-ray in a state in which the three optical axes are placed coaxially, and the controller 9 controls the measuring head shifting mechanism 8 on the basis of the measured height T of the sample S to adjust the distance with respect to the X-ray tube 2 and the X-ray detector 3 and, simultaneously, adjusts the focus position also for the observational system 5, the positioning of the irradiation point P1 of the sample S is achieved without necessity of the manual focus adjustment by an operator.

Also, when performing the calculation for the quantitative analysis by the controller 9 according to the difference between the standard position of irradiation P2 of the primary X-ray X1 and the heightwise position of the irradiation point P1, an accurate result of analysis is obtained without being affected by the changing distance by correcting the parameters to be used for the calculation according to the difference between the standard position of irradiation P2 and the height position of the irradiation point P1. In other words, an accurate result of analysis can be obtained in the analysis with the height of the sample S at the given irradiation point P1.

The triangulation-based laser displacement sensor 7 irradiates the sample S with the primary laser beam L1 and receives the secondary laser beam L2 returned therefrom. The height of the sample S is obtained by detecting the sensing state of the returned secondary laser beam L2 by the CCD type light receiving element (not shown) in the triangulation-based laser displacement sensor 7 (not shown) on an element to element basis. Accordingly, the height T of the sample S can be measured accurately without contact.

Furthermore, the triangulation-based laser displacement sensor 7 is capable of measuring the height T of the sample S in a state in which the sample S is placed on the sample stage 1. Therefore, the sample S on the sample stage 1 can be measured directly immediately before the analysis. Accordingly, the distance of the sample S with respect to the X-ray tube 2 and the X-ray detector 3 at the time of analysis can be obtained further accurately in comparison with the case where the height T of the sample S is measured before installing the sample stage 1.

The controller 9 also is capable of memorizing the height of the irradiation point P1. Therefore, by moving the sample stage 1 while irradiating the sample S with the primary laser beam L1, the height profile of the sample within a two-dimensional measuring range is obtained by acquiring the two-dimensional height data of the sample S.

The technical scope of the invention is not limited to the embodiments shown above, and various modifications may be made without departing the scope of the invention.

For example, although the triangulation-based laser displacement sensor is employed as a height measuring mechanism for the sample S in the embodiment described above, a linear regression-based laser displacement sensor may be employed as another example.

In this case, since the secondary laser beam is returned back coaxially with the primary laser beam, the surface area of the mirror can be reduced, and an adjustment mechanism can be simplified.

In the embodiment described above, the beam splitter 5b and the mirror 5c are configured to be movable and to be retractable from the course of the primary X-ray X1 at the time of analysis, so that the primary X-ray can be delivered to the sample without being attenuated in intensity. However, the invention is not limited thereto if real-time observation of the state of the sample during the irradiation with the primary X-ray is wanted. In this case, by using the beam splitter 5b and the mirror 5c having a thickness which minimizes the attenuation of the primary X-ray, the primary X-ray is allowed to pass through these members, so that the real time observation of the state of the sample during the irradiation with the primary X-ray is enabled.

The laser system which allows non-contact measurement is preferable as the height measuring mechanism as described above. However, a contact sensor may be employed as long as the sample is not affected thereby.

In the embodiment described above, the interior of the sample chamber is brought into a depressurized atmosphere for conducting the analysis. However, the analysis may be conducted in a state of not being in the vacuum (depressurized) atmosphere.

In the embodiment describe above, the energy dispersive fluorescence X-ray analysis apparatus has been described. However, the invention may be applied to other analyzing systems, for example, to a wavelength dispersive fluorescence X-ray analysis apparatus or an SEM-EDS (scanning electron microscope—energy dispersive X-ray analysis) apparatus which employs an electron beam as radiation to be irradiated and is capable of acquiring a secondary electronic image.

In the embodiment described above, the semiconductor detector is employed as the X-ray detector. However, the invention may be applied to a fluorescent X-ray thickness meter using a proportional counter tube instead.

What is claimed is:

1. An X-ray analysis apparatus comprising:
    a radiation source configured to irradiate an irradiation point on a sample with radiation;
    an X-ray detector configured to detect a characteristic X-ray and a scattered X-ray emitted from the sample and output a signal including energy information about the characteristic X-ray and the scattered X-ray;
    an analyzer configured to analyze the signal;
    a sample stage configured to allow placement of the sample thereon;
    a shifting mechanism being capable of relatively shifting the sample on the sample stage and the radiation source and the X-ray detector with respect to each other;
    a height measuring mechanism being capable of measuring the height of the irradiation point on the sample; and
    a controller configured to control the shifting mechanism on the basis of the measured height of the irradiation point on the sample and adjust the distance of the sample with respect to the radiation source and the X-ray detector.

2. The X-ray analysis apparatus according to claim 1, wherein the height measuring mechanism includes a laser displacement sensor.

3. The X-ray analysis apparatus according to claim 2, wherein the laser displacement sensor employs a triangulation-based system.

4. The X-ray analysis apparatus according to claim 2, wherein the optical axis of the radiation irradiated from the radiation source and the optical axis of the laser displacement sensor are coaxial, and the sample is irradiated with the radiation and a laser emitted from the laser displacement sensor.

5. The X-ray analysis apparatus according to claim 1 comprising:
    a sample observation system configured to observe the sample; and
    a focus switching drive mechanism configured to switch the focus of the sample observation system, wherein
    the focus position of the sample observation system is adjusted by controlling the focus switching drive mechanism on the basis of the height of the irradiation point on the sample measured by the height measuring mechanism.

6. The X-ray analysis apparatus according to claim 5, wherein the optical axis of the radiation irradiated from the radiation source, the optical axis of the sample observation system having the focus switching drive mechanism, and the optical axis of a laser displacement sensor are coaxial with respect to each other, and the sample is irradiated with the radiation and a laser emitted from the laser displacement sensor.

7. The X-ray analysis apparatus according to claim 6 comprising:
    a mirror configured to align the optical axis of the laser displacement sensor in coaxial with the optical axis of the radiation, and
    a beam splitter configured to align the optical axis of the radiation, the optical axis of the laser displacement sensor, and the optical axis of the sample observation system in coaxial with each other.

8. The X-ray analysis apparatus according to claim 1, wherein the height measuring mechanism is capable of measuring the height of the irradiation point on the sample in a state in which the sample is placed on the sample stage.

9. An X-ray analysis method for irradiating an irradiation point on a sample with radiation from a radiation source, detecting a characteristic X-ray and a scattered X-ray emitted from the sample by an X-ray detector, outputting a signal including energy information about the characteristic X-ray and the scattered X-ray, and analyzing the signal by an analyzer comprising:
    measuring the height of the irradiation point on the sample by a height measuring mechanism; and
    positioning the irradiation point by relatively shifting the sample on a sample stage, the radiation source and the X-ray detector with respect to each other by a shifting mechanism, wherein
    the positioning the irradiation point includes controlling the shifting mechanism on the basis of the measured height of the irradiation point on the sample and adjusting the distance of the sample with respect to the radiation source and the X-ray detector by a controller.

10. The X-ray analysis method according to claim 9 comprising:
    focusing a sample observation system on the irradiation point by a focus switching drive mechanism, wherein
    the focusing on the irradiation point includes controlling the focus switching drive mechanism on the basis of the measured height of the irradiation point on the sample and adjusting the focus of the sample observation system on the sample by the controller.

11. An X-ray analysis method for irradiating an irradiation point on a sample with radiation from a radiation source, detecting a characteristic X-ray and a scattered X-ray emitted from the sample by an X-ray detector, outputting a signal including energy information about the characteristic X-ray and the scattered X-ray, and analyzing the signal by an analyzer comprising:
  measuring the height of the irradiation point on the sample by a height measuring mechanism; and
  conducting measurement and analysis by delivering radiation at the height of the irradiation point on the sample, wherein
  the conducting measurement and analysis includes correcting parameters used in calculation according to the difference between a standard position of irradiation of the radiation and the heightwise position of the irradiation point when performing the calculation for a quantitative analysis from data obtained by the analyzer.

* * * * *